US009624384B2

(12) United States Patent
Mason et al.

(10) Patent No.: US 9,624,384 B2
(45) Date of Patent: Apr. 18, 2017

(54) WATER STABLE ANTIMICROBIAL SILANOL QUATERNARY AMMONIUM COMPOUNDS

(71) Applicant: IndusCo, Ltd., Greensboro, NC (US)

(72) Inventors: Joseph E. Mason, Belews Creek, NC (US); Dennis Victor Neigel, Salisbury, NC (US)

(73) Assignee: IndusCo, Ltd., Greensboro, NC (US)

( * ) Notice: Subject to any disclaimer, the term of this patent is extended or adjusted under 35 U.S.C. 154(b) by 0 days.

(21) Appl. No.: 14/680,689

(22) Filed: Apr. 7, 2015

(65) Prior Publication Data

US 2016/0295858 A1    Oct. 13, 2016

(51) Int. Cl.
*A01N 55/00* (2006.01)
*C09D 5/14* (2006.01)
*A01N 33/12* (2006.01)

(52) U.S. Cl.
CPC .............. *C09D 5/14* (2013.01); *A01N 33/12* (2013.01); *A01N 55/00* (2013.01)

(58) Field of Classification Search
CPC ................... A01N 5/005; A01N 55/00
See application file for complete search history.

(56) References Cited

U.S. PATENT DOCUMENTS

| | | | |
|---|---|---|---|
| 2,005,008 A | 6/1935 | Schaer | |
| 3,560,385 A | 2/1971 | Roth | 252/49.6 |
| 3,730,701 A | 5/1973 | Isquith et al. | 71/67 |
| 3,794,736 A | 2/1974 | Abbott et al. | 424/78 |
| 3,860,709 A | 1/1975 | Abbott et al. | 424/184 |
| 3,865,728 A | 2/1975 | Abbott et al. | 210/169 |
| 4,005,025 A | 1/1977 | Kinstedt | 252/89 R |
| 4,005,028 A | 1/1977 | Heckert et al. | 252/99 |
| 4,005,030 A | 1/1977 | Heckert et al. | 252/140 |
| 4,161,518 A | 7/1979 | Wen et al. | 424/52 |
| 4,282,366 A | 8/1981 | Eudy | 556/413 |
| 4,361,273 A | 11/1982 | Levine et al. | 236/11 |
| 4,393,378 A | 7/1983 | Danielsen et al. | 340/744 |
| 4,394,378 A | 7/1983 | Klein | 424/184 |
| 4,406,892 A | 9/1983 | Eudy | 424/184 |
| 4,421,796 A | 12/1983 | Burril et al. | 427/387 |
| 4,467,013 A | 8/1984 | Baldwin | 428/289 |
| 4,564,456 A | 1/1986 | Homan | 210/698 |
| 4,567,039 A | 1/1986 | Stadnick et al. | 132/70 |
| 4,615,882 A | 10/1986 | Stockel | 424/80 |
| 4,682,992 A | 7/1987 | Fuchs | 55/279 |
| 4,781,974 A | 11/1988 | Bouchette et al. | 428/288 |
| 4,797,420 A | 1/1989 | Bryant | 514/643 |
| 4,847,088 A | 7/1989 | Blank | 424/404 |
| 4,908,355 A | 3/1990 | Gettings et al. | 514/63 |
| 5,013,459 A | 5/1991 | Gettings et al. | 210/764 |
| 5,411,585 A | 5/1995 | Avery et al. | 106/287.1 |
| 5,954,869 A | 9/1999 | Elfersy et al. | 106/287.16 |
| 6,110,474 A * | 8/2000 | Roman | A61K 8/97 132/320 |
| 6,376,696 B1 | 4/2002 | Raab et al. | 556/423 |
| 6,613,755 B2 | 9/2003 | Peterson et al. | 514/63 |
| 6,632,805 B1 | 10/2003 | Liebeskind et al. | 514/63 |
| 2005/0008613 A1 | 1/2005 | Peterson et al. | 424/78.27 |
| 2008/0181862 A1 | 7/2008 | Chisholm et al. | 424/78.37 |
| 2013/0030207 A1 | 1/2013 | Taralp | 556/413 |

FOREIGN PATENT DOCUMENTS

| | | | |
|---|---|---|---|
| CA | 1217004 | 1/1987 | ............ C11D 3/395 |
| JP | 20091008 | 4/2013 | |
| WO | WO9741729 | 11/1997 | |
| WO | WO0078770 | 12/2000 | ............... C07F 7/18 |
| WO | WO 2011119237 A2 * | 9/2011 | ............ A01N 33/12 |
| WO | PCT/IB2010/051747 | 9/2013 | ............... C07F 7/04 |

OTHER PUBLICATIONS

Traber, M.G., et al. "Vitamin E: function and metabolism," FASEB Journal. (Jul. 1999), vol. 13, pp. 1145-1155.*
Sabine, J.R., et al. "Laboratory Evaluation of some Marine Plants on South Australian Beaches." J. Agric. Sci. Technol. (2001), vol. 3: pp. 91-100.*

* cited by examiner

Primary Examiner — Noble Jarrell
Assistant Examiner — John S Kenyon
(74) *Attorney, Agent, or Firm* — Tuggle Duggins P.A.; Blake Hurt

(57) ABSTRACT

A method of stabilizing aqueous solutions of antimicrobial silanol quaternary ammonium compounds (SQACs) from premature polymerization where the stabilizing agent is selected from a list of antimicrobial, naturally occurring, renewable, volatile, liquid phytochemical essential oils that easily form crystal clear microemulsions when water is added to the concentrated SQAC/essential oil mixture. These non-foaming oil-in-water microemulsions have excellent long term storage stability, remain very low in viscosity and do not phase or precipitate for many months. Many essential oils found to be useful in this process are non-toxic food additives having pleasant scents, have low flammability yet are volatile enough to evaporate upon cure down of the SQAC, resulting in a higher concentration of SQAC in the cured, antimicrobial film. Economically shippable concentrations of stabilized SQACs can be further diluted with water to application concentrations without losing any stabilizing properties and remain storage stable at these lower concentrations indefinitely.

12 Claims, 7 Drawing Sheets

WATER STABLE ANTIMICROBIAL SILANOL QUATERNARY AMMONIUM COMPOUNDS

BACKGROUND

Field

The present invention relates to antimicrobial silanol quaternary ammonium compounds (SQACs) and a method for controlling the viscosity stability of aqueous dilutions of SQACs using naturally derived, renewable, volatile, phytochemical essential oils.

Related Art

A biocide is any substance that kills microorganisms such as bacteria, molds, algae, fungi or viruses. A biostatic is any substance that inhibits the growth of these organisms. The collective group is called antimicrobials. People have been utilizing antimicrobials, commonly called preservatives, since they first discovered a need to extend the useful life of their food as well as their possessions. Sea salt may have been the first antimicrobial used to preserve food. The mummification techniques employed by early Egyptians used to preserve the human and animal body used salts and a variety of resins. These preservatives were thought to possess magical powers, as well as the ability to install qualities of eternal life.

The existence of microorganisms in nature was discovered in the late 1600s with the invention of the microscope. As early as 1705, mercuric chloride was used to preserve ships' planking against shipworm. It was not until the 19th century discoveries by Pasteur, Gram and others that the causative agents of microbiological deterioration were understood, although use of antimicrobials in a cause and effect relationship with microorganisms is still less than a century old.

Certain silanol quaternary ammonium compounds ("SQACs") possess bacteriostatic, fungistatic and algaestatic and/or bactericidal, fungicidal and algaecidal properties. For example, 3-(trimethoxysilyl)propyl octadecyldimethyl ammonium chloride is a commercial antimicrobial product marketed by Dow Corning as "BIOGUARD Q 9-5700". A number of other organosilicon amines and salts also exhibit antimicrobial activity.

Reactive silanols are able to bond with a variety of target surfaces because they form a covalent bond with any surface containing oxygen, nitrogen or carbon in any form. For example, hydroxides or oxides on the surfaces of metals (including stainless steel) will form a durable bond. In addition, silanol groups will homopolymerize via a condensation mechanism to form a durable, 3 dimensional cross-linked polymer matrix. Reactive silanols are therefore able to bond with surfaces such as plastic, metal, fabric, tile, masonry, vinyl, wood, painted surfaces and human skin.

When silanols are modified with biocidal adjuncts in the form of alkyl quaternary ammonium groups, and the silanols are fixed onto a surface, the active biocidal sites become fixed too. The films created are extremely thin, between 15 nm and 180 nm, and therefore the original physical properties of the surface are little affected.

Silanols having biocidal adjuncts typically exhibit a mechanism of action whereby bacteria arriving on a treated surface will assimilate the biocidal adjunct's hydrocarbon, and the positively charged nitrogen atom will affect the electrical equilibrium of the cell. More specifically, the nitrogen atom disrupts the porin channels and/or outer protein layers, causing cell death.

The fixed nature of the biocide is important where toxicity, taint and other organoleptic aspects are of concern. This bactericidal surface treatment is not removed by normal cleaning procedures. In fact, it is important to maintain the normal cleaning regime in order to 'refresh' the biocidal surface. The thinness of the film enables application in areas where optical properties are important such as treatment of contact lenses. Silanols with biocidal adjuncts have been used in the treatment of bed sheets, hospital garments, curtains, floor and wall materials, air filtration systems, medical devices, bandages, surgical instruments and implants, and to prevent biofilm growth on catheters, stints, contact lenses and endrotracheal tubes.

Based toxicity information, the EPA concluded that there are no endpoints of concern for repeated oral or dermal exposure to the trimethoxysilyl quats. This conclusion was based on low toxicity observed in acute, subchronic and developmental studies conducted with the trimethoxysilyl quat compounds. They further concluded that there are no concerns for carcinogenicity for the trimethoxysilyl quats based on the results of the mutagenicity studies and the lack of any systemic toxicity in the toxicity database.

Based on hydrolysis data, the EPA has concluded that trimethoxysilyl quats are soluble but not stable in water. They stated that due the instability of the compounds and their formation of an insoluble silane degradate, that the trimethoxysilyl quats are not expected to contaminate surface or ground water due to rapid degradation by hydrolysis.

While aqueous SQACs have a tremendous amount of potential as antimicrobials, there are significant shortcomings. They are very unstable and have a short shelf life. For example, premature sedimentation of polysilsesquioxane-type polymers occurs in even low aqueous concentrations. Also, premature polymerization causes unwanted solution viscosity, thereby complicating conventional coating methods.

A variety of strategies have been employed in order to extend the storage life of aqueous SQACs. Examples include introducing surfactant additives, to coordinate the free silanol ends with stabilizers such as simple sugars and other multiple hydroxyl group molecules; coordinating and associating said quaternary organosilane hydrolysates with hydrophilic polymers; incorporating non-aqueous solvents such as the toxic methanol and methyl or butyl cellosolve, using alternative aqueous/organic systems, and combinations thereof. In some cases, pH adjustments have been used to maximize the benefits imparted by a stabilizer. These strategies all have shortcomings including undesirably creating a hydrophilic toxicity and cost.

It is desirable that the aqueous medium contains additives and components that eliminate or decrease the premature homopolymerization of the hydrolyzed silanol groups, thereby increasing storage stability. It is desirable that the aqueous medium contains additives and components that eliminate or decrease unwanted increases in viscosity arising from premature homopolymerization. It is desirable that the aqueous medium contains additives and components that eliminate or decrease unwanted precipitation arising from premature homopolymerization. It is also desirable that the aqueous medium contains additives and components that impart a pleasant scent, maintain solution clarity, improve performance of the underlying SQAC, and protect the composition against aqueous mold growth. It is desirable that the additives will evaporate completely during the coating and curing operation, thus allowing the generation of a high degree of homopolymer crosslinking of the silanol groups, thereby providing a highly water and solvent insoluble coating on the substrate. It is desirable that the additives are not hydrophilic and that they do no alter the cationic charge density of the SQAC. It is also desirable that the additives and components are environmentally friendly.

In short, it is desirable to employ SQAC stabilizers having the following characteristics: 1) Low Toxicity; 2) Low Flammability; 3) Excellent stabilization of aqueous SQACs; 4) Pleasant scent; 5) Volatility (little or no incorporation of the stabilizer into the cured film); 6) Antimicrobial Activity; and 7) Obtained from a renewable resource.

Unexpectedly, a unique group of volatile essential oil stabilizers has been discovered that satisfies all 7 of the above attributes needed to correct the shortcomings of previous inventions of this type. These unique stabilizers are certain naturally derived, renewable, volatile, phytochemical essential oils (essential means "having an essence") that have been proven to possess low toxicity, low flammability, excellent stabilization of aqueous SQACs, pleasant scent, good volatility, and demonstrate antimicrobial activity of their own.

SUMMARY

This invention is a method of stabilizing aqueous solutions of antimicrobial silanol quaternary ammonium compounds (SQACs) where the stabilizing agent is chosen from the collective group of volatile essential oils that are commonly obtained by steam distillation or cold pressing of stems, bark, leaves, fruit, peels and flowers of various plants species throughout the world. Some of the preferred essential oils used in the instant invention are derived from leaves that are edible herbs. Other preferred essential oils are extracted from the peels of citrus fruits that are used as flavorings for food and beverages. This source of these stabilizing agents is plentiful, renewable and generally considered to have low toxicity to humans and animals. The method process of this invention teaches the manufacture of crystal clear, water stabilized SQAC microemulsions that show little or no sign of 2nd degree homopolymerization (viscosity increase) of 3rd degree homopolymerization (polymer precipitation) when aged at room temperature for several months at SQAC assays that allow for good transportation economics and excellent utility in use when further diluted.

These and other aspects of the present inventions will become apparent to those skilled in the art after a reading of the following description of the preferred embodiment when considered with the drawings.

DESCRIPTION OF THE EMBODIMENTS

Figure 1:
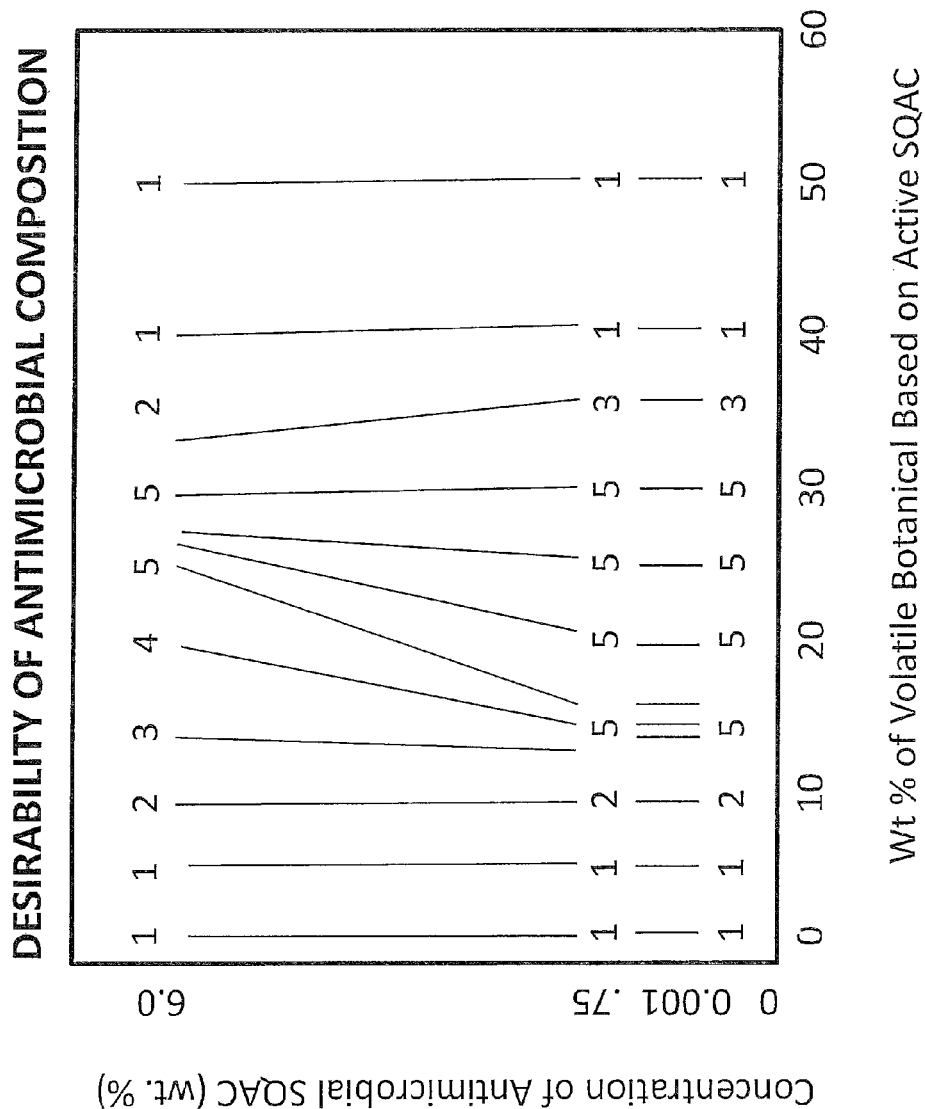
FIG. 1 is a graphical representation of the expected overall stability effectiveness of antimicrobial compositions prepared according to the present invention as a function of the concentration of volatile essential oil and the concentration of silanol quaternary ammonium compound in water.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

As used herein, the following terms apply:

"Botanical" or "Phytochemical" is a substance derived from a plant, such as an essential oil.

"Stable" shall mean no phase separation, precipitation, turbidity values of <40 NTU and viscosity of <50 cPs at 6% active SQAC in water for at least 3 months at 25 C.

"SQAC" is a silanol quaternary ammonium compound. Preferred examples discussed herein are designated as SQAC #1-3.

"SQAC #1" is 3-(trimethoxysilyl) propyl-N-octadecyl-N, N-dimethyl ammonium chloride.

"SQAC #2" is 3-(trimethoxysilyl) propyl-N-tetradecyl-N, N-dimethyl ammonium chloride.

"SQAC #3" is 3-(trihydroxysilyl) propyl-N-octadecyl-N, N-dimethyl ammonium chloride.

SQAC #1 is commercially available from Indusco, Ltd located in Greensboro, N.C. as Bioshield 7200 and sold as a concentrated solution of the active ingredient in anhydrous methanol. A similar product is available from both Dow Corning and Microban International and others. Of the three selected SQAC compounds, SQAC #1 is one acceptable compound for demonstrating the process of these inventions due to its high sales volume and popularity of use as an antimicrobial coating on a myriad of substrates.

The processes of the present invention produce novel, crystal clear, viscosity stable, oil-in-water microemulsions using SQACs, phytochemical essential oils, and distilled or deionized water. Compositions of the present invention are considered stable in water. Microemulsion technology has been in existence for many years. In fact, many commercial microemulsion products are found in the marketplace including floor polishes and cleaners, personal care products, pesticide delivery systems, cutting oils and drug delivery systems. Microemulsions are crystal clear because the micellar particle size is too small to scatter visible light. The IUPAC definition of microemulsion is "a dispersion of water, oil and surfactant(s) that is an isotropic and thermodynamically stable system with dispersed domain diameter varying approximately from 1 to 100 nm, usually 10 to 50 nm." The aqueous phase may contain salts or other ingredients such as polar solvents, and the oil may be a complex mixture of organic compounds. In contrast to ordinary, white macroemulsions that usually require high shear conditions to form, microemulsions form upon simple mixing of the components, without the need for high-energy homogenization. Also, microemulsions of the present invention are stable against phase separation.

SQAC is an active ingredient that produces durable antimicrobial films when cured. Unexpectedly, SQAC is able to form a microemulsion with phytochemical essential oils without any need for additional surfactants or organic solvents. Such microemulsions need only standard mixing requirements such as those found in low speed mixing vessels, not high shear equipment such as various types of high speed or high-pressure homogenizers. These microemulsions have been developed on lab scale using only the shear of low speed magnetic stirring bar mixing.

It has also been found according to the present invention that when preparing these microemulsions, order of addition is quite important. The SQAC is first to be added to the mixing vessel as a concentrated solution in the reaction solvent, followed by adding the essential oil, which dissolves in the concentrated SQAC to form a low viscosity, easily mixable, clear solution. The addition of the essential oil will lower the temperature at which partial insolubility of the SQAC occurs, similarly to what would be expected if more reaction solvent was added. Mixtures of SQAC and essential oil have been stored at room temperature for several months and show no signs of precipitation, loss of activity, color change or their ability to form microemulsions when water is mixed in.

To accomplish the processes of making a crystal clear, viscosity stable emulsion, the distilled or deionized water is added to the SQAC/essential oil solution under moderate agitation. Depending upon the type of SQAC and essential oil being used, the applicants did also discover that water heated above room temperature produces clear microemulsions more quickly. However, choosing a process water temperature depends in part on the boiling point of the SQAC/essential oil/polar solvent mixture being treated based on safety considerations.

The rate of water addition also has been found by the applicant to be dependent upon the components being used. Some systems allow water addition rates as rapid as less than one minute, while other systems require a water addition rate that will maintain a clear microemulsion mixing in the vessel. Microemulsion systems will maintain this clear appearance throughout the water addition process. This is one embodiment for carrying out the process of these inventions. If any turbidity of the mixing vessel contents occurs, there is a good chance a microemulsion will not be formed to completion resulting in less than crystal clarity of the final dispersion. Cloudy microemulsions may be repaired to form clear microemulsions by post heating the fully diluted microemulsion, then stopping the agitation and allowing the microemulsion to slowly cool to room temperature.

Although most of the aging stability studies were performed on economically shippable SQAC concentrations of 6% to 8% (active basis), further dilution with water produced crystal clear, stable microemulsions all the way down to application strength of 0.1% to 5.9% (active basis) SQAC concentrations. Stability against precipitation remained excellent through this entire dilution range.

The present invention can best be understood after a review of the following examples:

Example 1

Into an 8 oz. glass jar was weighed 16.67 g of Bioshield 7200 (72% active SQAC) followed by 3.60 g of tea tree essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of tea tree oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 40 cPs and 5 Nephelos Turbidity Units (NTU).

Example 2

Into an 8 oz. glass jar was weighed 16.67 g of Bioshield 7200 (72% active SQAC) followed by 2.22 g of peppermint essential oil and stirred on a magnetic stirring plate until the two components were clear and uniform (~1 min). With continued moderate stirring, 181.11 g of distilled water at a temperature of 35 C to 45 C was rapidly poured into the jar. Stirring was continued as the transparent concentrate slowly dissolved in the water to form a crystal clear microemulsion of peppermint oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 8 months aging at 25 C this sample was measured at 20 cPs and 33 NTU.

Example 3

Into an 8 oz. glass jar was weighed 16.67 g of Bioshield 7200 (72% active SQAC) followed by 2.18 g of Thyme essential oil (*T. vulgaris*) and stirred on a magnetic stirring plate until the two components were clear and uniform (~1 min). With continued moderate stirring, 181.15 g of distilled water at a temperature of 35 C to 45 C was rapidly poured into the jar. Stirring was continued as the transparent concentrate slowly dissolved in the water to form a crystal clear microemulsion of thyme oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 6 months aging at 25 C this sample was measured at 24 cPs and 30 NTU.

Example 4

Into an 8 oz. glass jar was weighed 16.67 g of Bioshield 7200 (72% active SQAC) followed by 3.60 g of grapefruit essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of grapefruit oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 12 cPs and 10 NTU.

Example 5

Into an 8 oz. glass jar was weighed 16.67 g of Bioshield 7200 (72% active SQAC) followed by 3.60 g of orange essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of orange oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 22 cPs and 5 NTU.

Example 6

Into an 8 oz. glass jar was weighed 16.67 g of Bioshield 7200 (72% active SQAC) followed by 3.60 g of lime essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of lime oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 32 cPs and 12 NTU.

Example 7

Into an 8 oz. glass jar was weighed 16.67 g of Bioshield 7200 (72% active SQAC) followed by 3.60 g of tangerine essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of tangerine oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 16 cPs and 5 Nephelos Turbidity Units (NTU).

Example 8

Into an 8 oz. glass jar was weighed 16.67 g of Bioshield 7200 (72% active SQAC) followed by 3.60 g of lemon essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of lemon oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 16 cPs and 5 Nephelos Turbidity Units (NTU).

Example 9

Into an 8 oz. glass jar was weighed 16.67 g of Bioshield 7200 (72% active SQAC) followed by 3.60 g of pine essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of pine oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 18 cPs and 9 NTU.

Example 10

Into an 8 oz. glass jar was weighed 16.67 g of Bioshield 7200 (72% active SQAC) followed by 3.60 g of cedarwood essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of cedarwood oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 4 cPs and 5 NTU.

Comparative Example 11

Into an 8 oz. glass jar was weighed 16.67 g of Bioshield 7200 (72% active SQAC) followed by NO essential oil. With moderate stirring, 183.33 g of distilled water at a temperature of 35 C to 45 C was rapidly poured into the jar. Stirring was continued as the transparent concentrate slowly dissolved in the water to form a crystal clear solution of a 6.0% active Bioshield. Brookfield viscosity of the freshly prepared solution was measured at 10 cPs at 25 C and the pH was measured at 3.6 without any adjustment. The jar was sealed and placed in a 25 C static oven and analyzed daily for both viscosity increase (linear condensation polymerization) and development of insoluble precipitation (3 dimensional crosslinking) as measured by Hach Ratio Turbidimetry. After 13 days aging at 25 C this sample was measured at 630 cPs and 100 NTU, exceeding both storage stability limits set for these parameters.

A summary of findings of the Examples is set forth in TABLE 1:

TABLE 1

EFFECT OF BOTANICALS ON TURBIDITY AND VISCOSITY OF AGED SQAC COMPOSITIONS

| | | | | INITIAL | | | AFTER AGING | | |
|---|---|---|---|---|---|---|---|---|---|
| SQAC (g) | BOTANICAL | BOTANICAL (g) | WATER (g) | TURBIDITY (NTU) | VISCOSITY (cPs) | pH | TURBIDITY (NTU) | VISCOSITY (cPs) | AGE (months) |
| 16.67 | Tea tree | 3.6 | 179.73 | 1 | 10 | 3.7 | 5 | 40 | 3 |
| 16.67 | Peppermint | 2.22 | 181.11 | 1 | 10 | 3.7 | 33 | 20 | 8 |
| 16.67 | Thyme | 2.18 | 181.15 | 1 | 10 | 3.7 | 30 | 24 | 6 |
| 16.67 | Grapefruit | 3.6 | 179.73 | 1 | 10 | 3.7 | 10 | 12 | 3 |
| 16.67 | Orange | 3.6 | 179.73 | 1 | 10 | 3.7 | 5 | 22 | 3 |
| 16.67 | Lime | 3.6 | 179.73 | 1 | 10 | 3.7 | 12 | 32 | 3 |
| 16.67 | Tangerine | 3.6 | 179.73 | 1 | 10 | 3.7 | 5 | 16 | 3 |
| 16.67 | Lemon | 3.6 | 179.73 | 1 | 10 | 3.7 | 5 | 16 | 3 |
| 16.67 | Pine | 3.6 | 179.73 | 1 | 10 | 3.7 | 9 | 18 | 3 |
| 16.67 | Cedarwood | 3.6 | 179.73 | 1 | 10 | 3.7 | 5 | 4 | 3 |
| 16.67 | Orange Peel | 3.6 | 179.73 | 1 | 10 | 3.7 | 8 | 18 | 3 |
| 16.67 | NONE | 0 | 183.33 | 1 | 10 | 3.6 | 100 | 630 | 0.43 |

FIG. 1 graphically represents the overall stability effectiveness of SQAC/essential oil microemulsions as a function of the concentration of volatile essential oil and the concentration of silanol quaternary ammonium compound. This is shown in the form of a surface response curve illustrating the interplay of the concentration of the SQAC and essential oil on the stability effectiveness of the composition, including turbidity, viscosity and phase separation. More specifically, compositions were rated 5 if they were expected to be "superior". Compositions were rated 4 if they were expected to be "good". Compositions were rated 3 if they were expected to be "acceptable". Compositions were rated 2 if they were expected to be "poor". Compositions were rated 1 if they were expected to be "unacceptable". As can be seen, there is a "sweet spot" for achieving the most desirable composition, as indicated by the 5's. Indeed even very low concentrations of antimicrobial SQAC's are beneficial.

This surface response curve is set forth on data of TABLE 2:

TABLE 2

| Wt % Volatile Botanical on Active SQAC | Desirability @ 0.75% Active SQAC | Desirability @ 6.0% Active SQAC |
|---|---|---|
| 0 | 1 | 1 |
| 5 | 1 | 1 |
| 10 | 2 | 2 |
| 15 | 5 | 3 |
| 20 | 5 | 4 |
| 25 | 5 | 5 |
| 30 | 5 | 5 |
| 35 | 3 | 2 |
| 40 | 1 | 1 |
| 50 | 1 | 1 |

Figure 2:
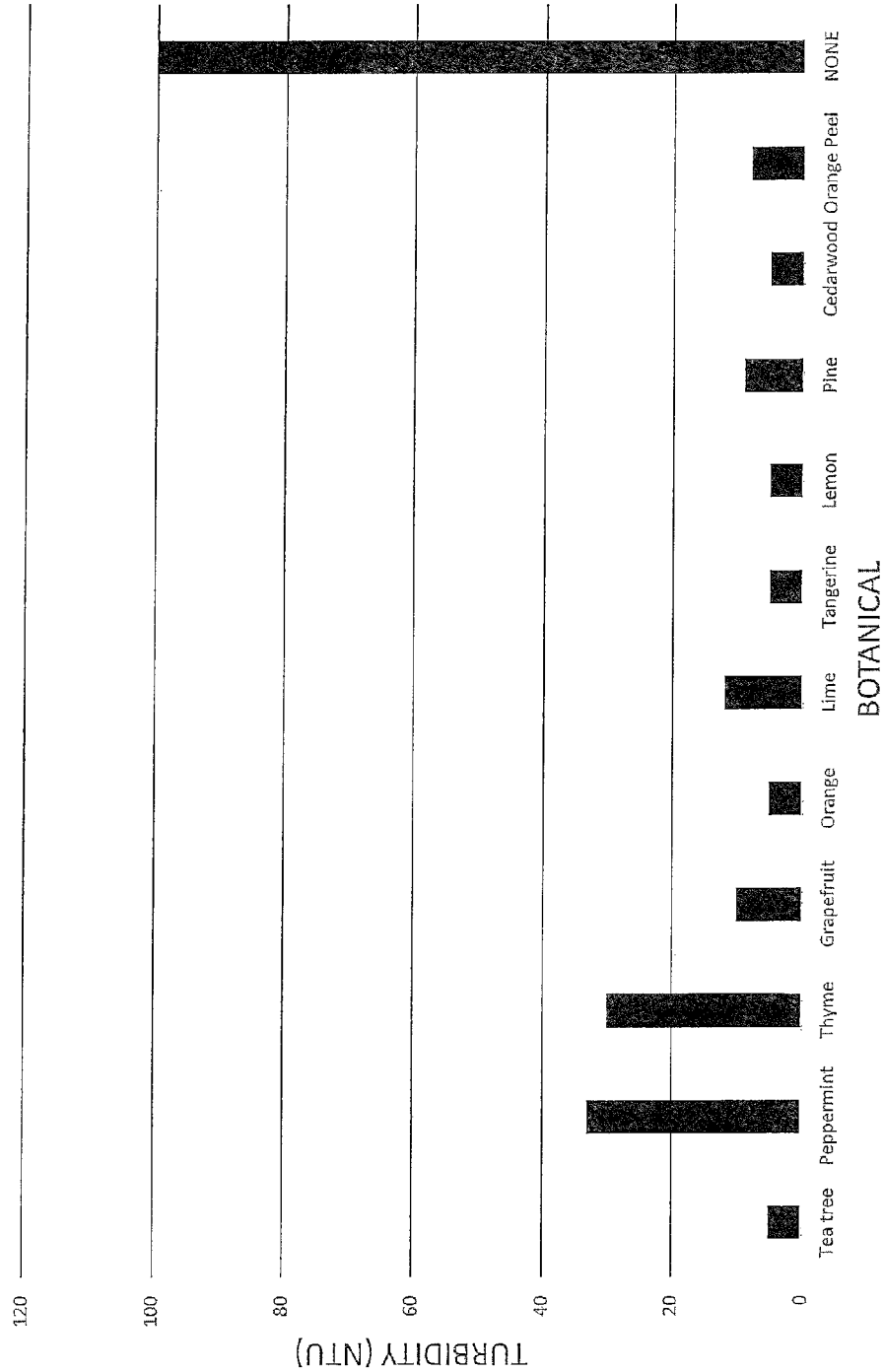
FIG. 2 illustrates the turbidity due to precipitation of insoluble SQAC polymer of various SQAC essential oil microemulsions compared to a composition having no essential oil.

As shown in FIG. 2, aged compositions of SQAC/essential oil microemulsions exhibit substantially lower turbidity than the aged composition having no essential oil. The data corresponding to this graph is set forth in TABLE 1. It is important to note that the negative control ("NONE") was aged only 13 days, while the test samples were aged 3-8 months.

Figure 3:
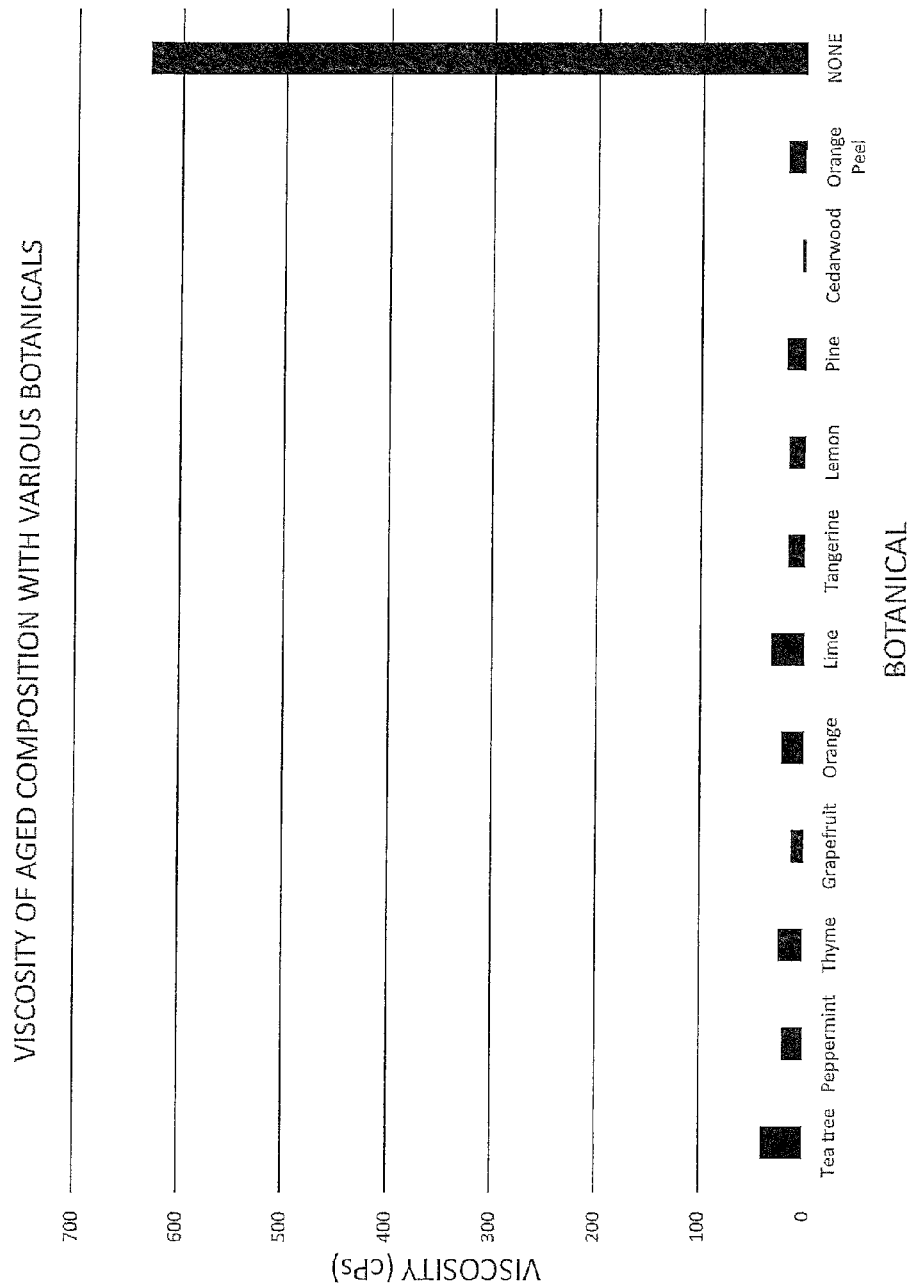
FIG. 3 illustrates the viscosity of various SQAC/essential oil microemulsions compared to a composition having no essential oil.
Figure 4:
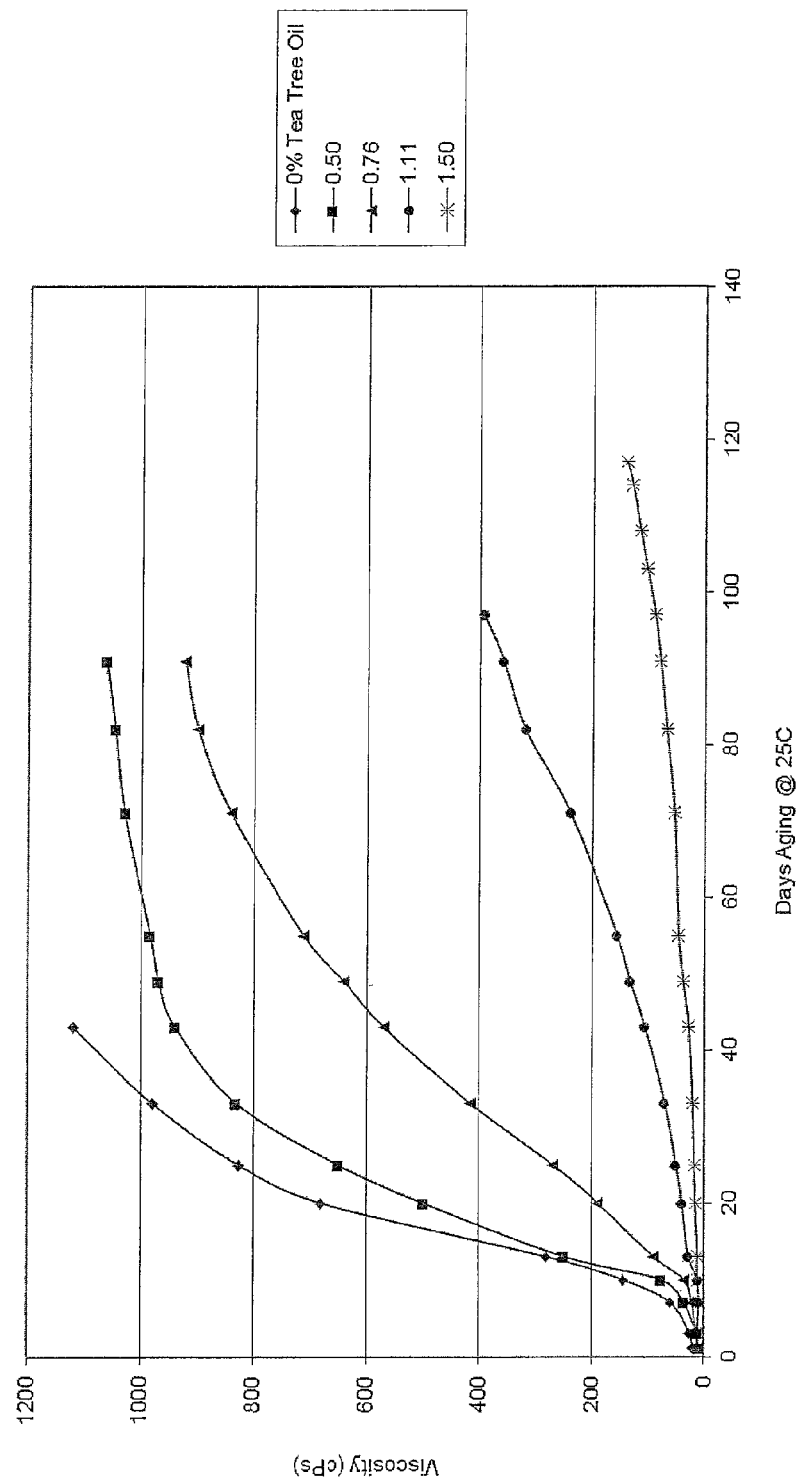
FIG. 4 demonstrates the viscosity of SQAC/Tea Tree Oil microemulsions over time compared to a composition having no Tea Tree Oil.
Figure 5:
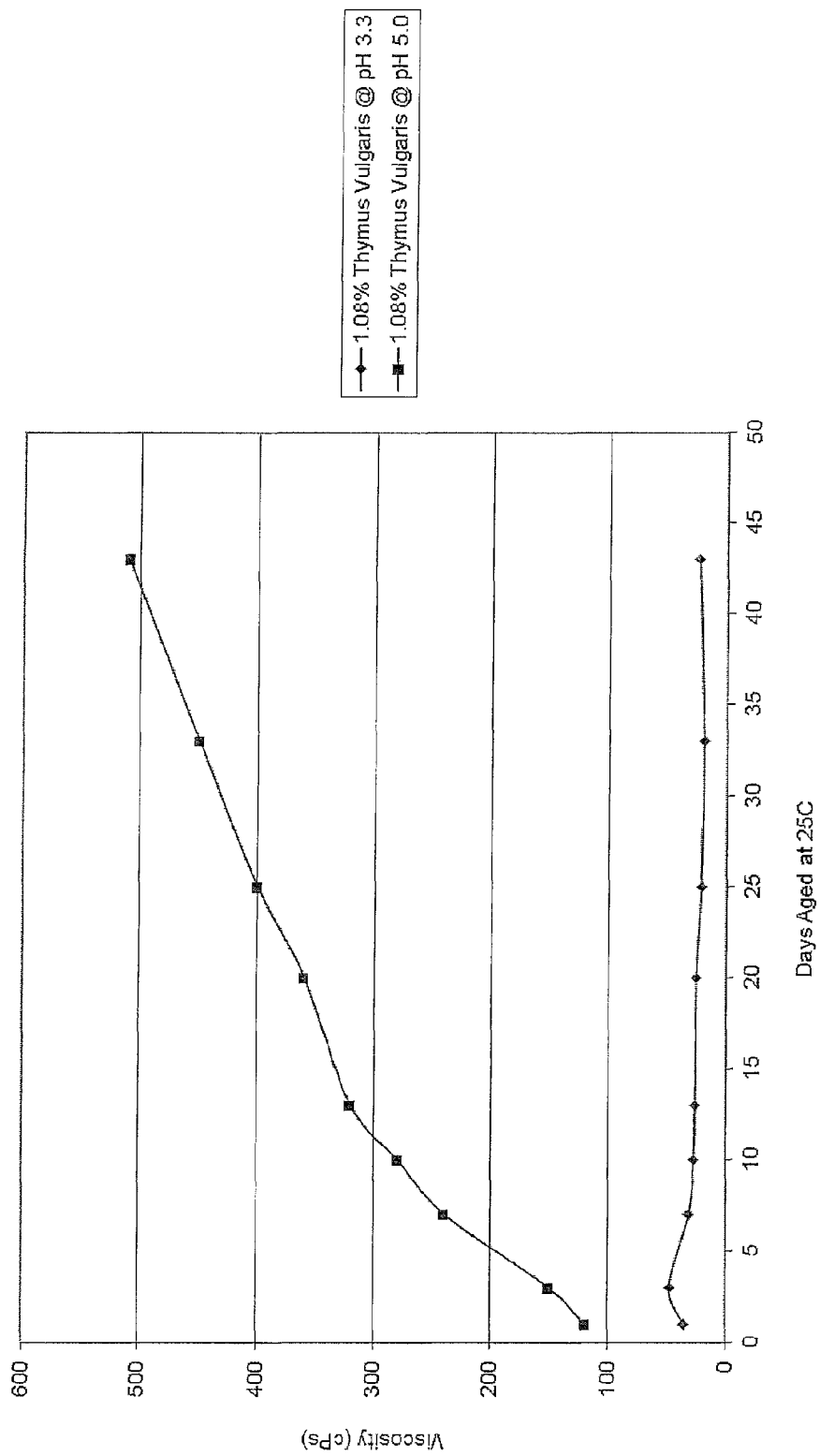
FIG. 5 demonstrates the viscosity of SQAC/Thyme Essential Oil microemulsions over time compared to a composition having no Thyme Essential Oil.

As shown in FIG. 3, aged compositions of SQAC/essential oil microemulsions exhibit substantially lower viscosity than the aged composition having no essential oil. The data corresponding to this graph is set forth in TABLE 1. It is important to note that the negative control ("NONE") was aged only 13 days, while the test samples were aged 1-8 months.

Figure 6:
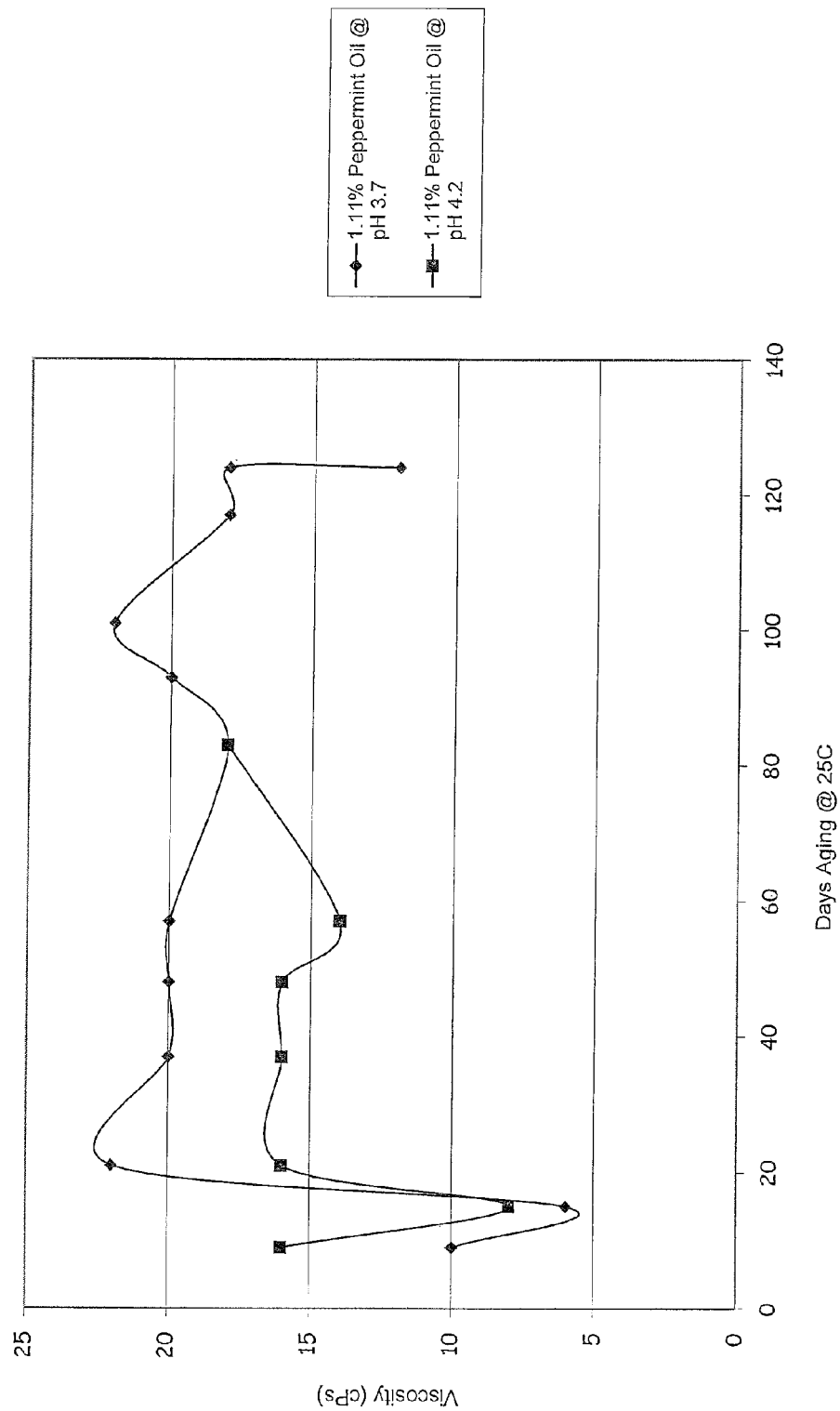
FIG. 6 demonstrates the viscosity of the same concentration of SQAC/peppermint essential oil at two different pHs.
Figure 7:
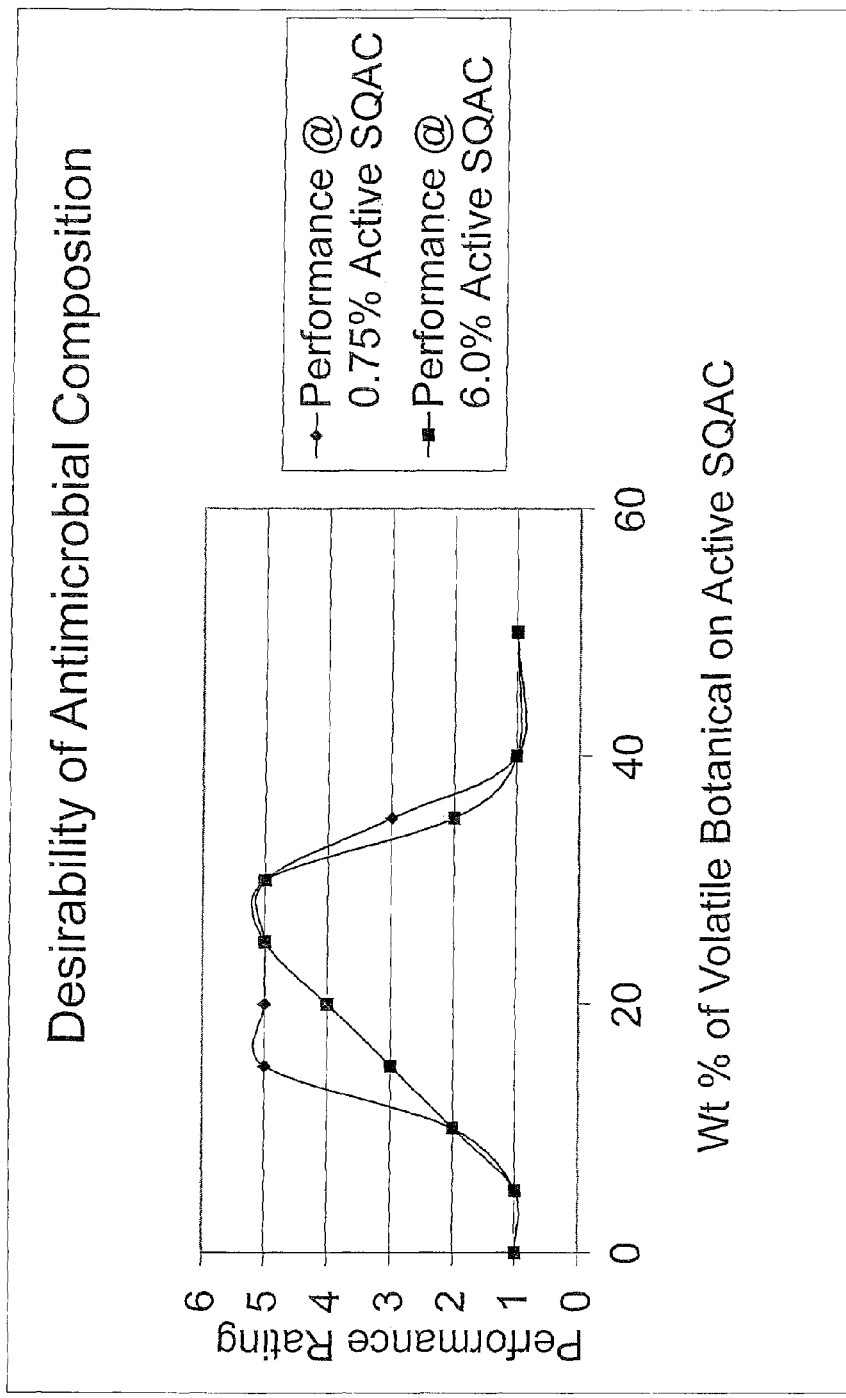
FIG. 7 depicts the aqueous stability of both a 0.75% and a 6.0% solution of SQAC as a function of ratio of volatile botanical to SQAC.

FIG. 6 depicts demonstrates the viscosity of the same concentration of peppermint oil at pH of 3.7 and 4.2. The 4.2 pH sample fully precipitated out after 80 days, so there was no viscosity or data charted after 80 days.

We claim:

1. A stabilized aqueous solution resistant to premature polymerization comprising:
    a mixture formed from a 3-(trihydroxysilyl) propyl-N-octadecyl-N,N-dimethyl ammonium chloride compound and an orange oil essential oil; and
    a balance of demineralized water to a desired aqueous concentration.

2. The stabilized aqueous solution of claim 1 wherein the 3-(trihydroxysilyl) propyl-N-octadecyl-N,N-dimethyl ammonium chloride compound is between about 0.1 wt. % and about 10 wt. % of the mixture.

3. The stabilized aqueous solution of claim 1 wherein the 3-(trihydroxysilyl) propyl-N-octadecyl-N,N-dimethyl ammonium chloride compound is between about 0.1 wt. % and about 1 wt. % of the mixture.

4. The stabilized aqueous solution of claim 1 wherein the 3-(trihydroxysilyl) propyl-N-octadecyl-N,N-dimethyl ammonium chloride compound is greater than about 0.2 wt. % of the mixture.

5. The stabilized aqueous solution of claim 1 wherein the ratio of a weight of the orange oil essential oil to the weight of the the 3-(trihydroxysilyl) propyl-N-octadecyl-N,N-dimethyl ammonium chloride compound is greater than about 0.15.

6. The stabilized aqueous solution of claim 1 wherein the ratio of a weight of the orange oil essential oil to the weight of the the 3-(trihydroxysilyl) propyl-N-octadecyl-N,N-dimethyl ammonium chloride compound is between about 0.2 and about 0.5.

7. The stabilized aqueous solution of claim 1 wherein the ratio of a weight of the orange oil essential oil to the weight of the the 3-(trihydroxysilyl) propyl-N-octadecyl-N,N-dimethyl ammonium chloride compound is about 0.3.

8. A stabilized aqueous solution resistant to premature polymerization comprising:

a mixture formed from an effective amount of a 3-(trihydroxysilyl) propyl-N-octadecyl-N,N-dimethyl ammonium chloride compound and an orange oil essential oil; and a balance of demineralized water to a desired aqueous concentration, wherein the mixture is formed in a reaction medium for mixing the 3-(trihydroxysilyl) propyl-N-octadecyl-N,N-dimethyl ammonium chloride compound and the orange oil essential oil before diluting with the water.

9. The stabilized aqueous solution of claim 8 wherein the reaction medium is a volatile organic reaction medium.

10. The stabilized aqueous solution of claim 9 wherein the volatile organic reaction medium is selected from a group consisting of aliphatic compounds.

11. The stabilized aqueous solution of claim 9 wherein the volatile organic reaction medium is an alcohol.

12. The stabilized aqueous solution of claim 11 wherein the alcohol is methanol.

* * * * *